Figure 1:
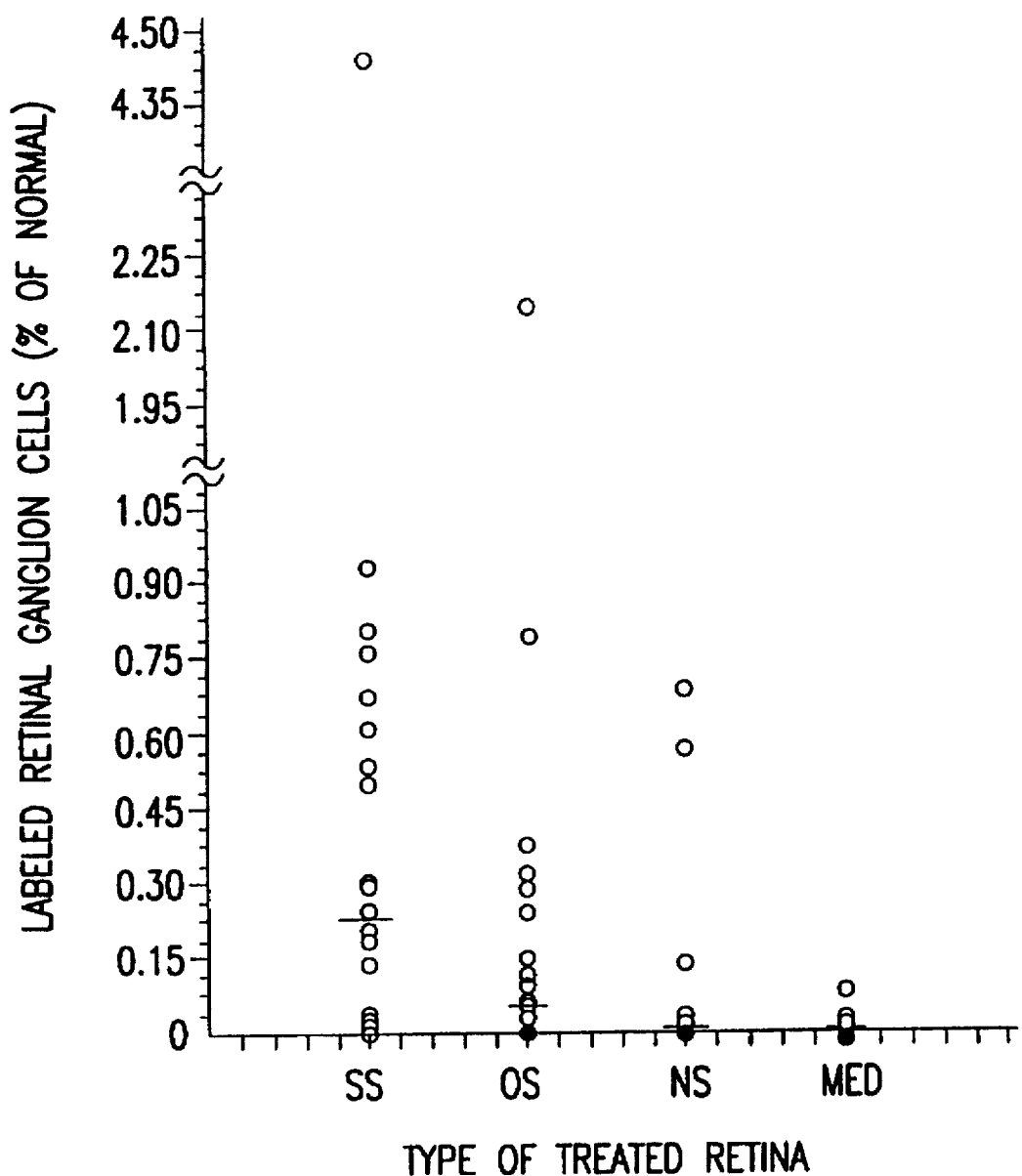

US005800812A

United States Patent [19]
Eisenbach-Schwartz et al.

[11] Patent Number: 5,800,812
[45] Date of Patent: Sep. 1, 1998

[54] METHODS OF USE OF MONONUCLEAR PHAGOCYTES TO PROMOTE AXONAL REGENERATION

[75] Inventors: Michal Eisenbach-Schwartz; Orly Spiegler, both of Rehovot, Israel; David L. Hirschberg, Stanford, Calif.

[73] Assignee: Yeda Research And Development Co. Ltd., Rehovot, Israel

[21] Appl. No.: 695,351

[22] Filed: Aug. 9, 1996

Related U.S. Application Data

[63] Continuation-in-part of Ser. No. 528,845, Sep. 15, 1995, abandoned.

[51] Int. Cl.$^6$ ............................................. C12N 5/06
[52] U.S. Cl. .................................................. 424/93.7
[58] Field of Search ................................ 424/93.7, 520, 424/570; 435/948

[56] References Cited

U.S. PATENT DOCUMENTS

| | | | |
|---|---|---|---|
| 5,078,996 | 1/1992 | Conlon et al. | 424/85.1 |
| 5,082,670 | 1/1992 | Gage et al. | 424/520 |
| 5,157,024 | 10/1992 | Gordon | 514/23 |

FOREIGN PATENT DOCUMENTS

| | | |
|---|---|---|
| 0 172 987 A2 | 3/1986 | European Pat. Off. . |
| 0 415 321 A1 | 3/1991 | European Pat. Off. . |
| 0 501 445 A1 | 9/1992 | European Pat. Off. . |

OTHER PUBLICATIONS

Perry et al. Curr. Op. Neurobiol. 2:679–682 (1992).
Barrett et al. Neurosci. Abstr. 15:317 (1989) (Abstract No. 125.12).
Barrett et al., Anat. Rec. 226: 11A (1990) (Abstract).
Blaugrund et al., 1993, "Axonal Regeneration Is Associated With Glial Migration: Comparison Between the Injured Optic Nerves of Fish and Rats", Journal of Comparative Neurology 330:105–112.
Cohen et al., 1990, "Oligodendrocyte cytotoxic factor associated with fish optic nerve regeneration: implications for mammalian CNS regeneration", Brain Research 537:24–32.
Eitan and Schwartz, 1993, "A Transglutaminase That Converts Interleukin–2 into a Factor Cytotoxic to Oligodendrocytes", Science 261:106–108.
Eitan et al., 1992, "Identification of an interleukin 2–like substance as a factor cytotoxic to oligodendrocytes and associated with central nervous system regeneration", Proc. Natl. Acad. Sci. USA 89:5442–5446.
Hirschberg and Schwartz, 1995, "Macrophage recruitment to acutely injured central nervous system is inhibited by a resident factor: a basis for an immune–brain barrier", Journal of Neuroimmunology 61:89–96.
Lavie et al., 1987, "Morphological response of injured adult rabbit opti nerve to implants containing media conditioned by growing optic nerves", Brain Research 419:166–172.
Schwartz, 1987, "Molecular And Cellular Aspects Of Nerve Regeration", CRC Critical Reviews In Biochemistry 22:89–110.

Schwartz et al., 1992, "Tumor Necrosis Factor and TNF–Like Factors in Central Nervous System Regeneration", in Tumor Necrosis Factor: Structure–Function Relationships and Clinical Application (Osawa and Bonavida, eds.), pp. 135–143.
Jackowski, 1995, "Neural injury repair: hope for the future as barriers to effective CNS regeneration become clearer", British J. Neurosurgery 9:303–317.
Danon et al., 1989, "Promotion of wound repair in old mice by local injection of macrophages," Proc. Natl. Acad. Sci. USA 86:2018–2020.
Heumann et al., 1987, "Differential regulation of mRNA encoding nerve growth factor and its receptor in rat sciatic nerve during development, degeneration, and regeneration: Role of macrophages", Proc. Natl. Acad. Sci. USA 84:8735–8739.
Ignatius et al., 1986, "Expression of apolipoprotein E during nerve degeneration and regeneration", Proc. Natl. Acad. Sci. USA 83:1125–1129.
Patrick et al., 1996, "Quantitative Effects of Peripheral Monocytes and Nerve Growth Factor on CNS Neural Morphometric Outgrowth Parameters in Vitro," Exp. Neurology 138:277–285.
Perry et al., 1987, "The Macrophage Response To Central and Peripheral Nerve Injury A Possible Role for Macrophages in Regeneration", J. Exp. Med. 165:1218–1223.
Perry and Gordon, 1991, "Macrophages and the Nervous System", International Review of Cytology 125:203–244.
Stoll et al., 1989, "Wallerian degeneration in the peripheral nervous system: participation of both Schwann cells and macrophages in myelin degradation", Journal of Neurocytology 18:671–683.
Lu and Richardson, 1991, "Inflammation near the Nerve Cell Body Enhances Axonal Regeneration", J. Neuroscience 11:972–978.
Blaugrund et al., 1992, "Disappearances of astrocytes and invasion of macrophages following crush injury of adult rodent optic nerves: Implications for regeneration", Exp Neurol 118:105–115.

(List continued on next page.)

Primary Examiner—Jean C. Witz
Attorney, Agent, or Firm—Pennie & Edmonds LLP

[57] ABSTRACT

Methods and compositions for the use of allogeneic mononuclear phagocytes to promote axonal regeneration in the central nervous system of a mammal are disclosed. In one embodiment, allogeneic mononuclear phagocytes are cultured together with stimulatory tissue, such as dermis or at least one nerve segment, and are subsequently administered into the central nervous system of a mammal at or near a site of injury or disease. In an alternative embodiment, autologous monocytes, preferably stimulated autologous monocytes, are administered into the central nervous system of a mammal at or near a site of injury or disease. Methods for identifying stimulatory tissue and cells and methods and compositions for cryopreserved allogeneic mononuclear phagocytes are also disclosed.

26 Claims, 11 Drawing Sheets

OTHER PUBLICATIONS

Chamak et al., 1994, "Brain macrophages stimulate neurite growth and regeneration by secreting thrombospondin", J Neurosci Res 38:221–233.

Chamak and Mallat, 1993, "Regulation of neurite growth and regeneration by brain macrophages: Involvement of thrombospondin", J Neurochem 61(Suppl.):S99 (Abstract #280018–3).

David et al., 1990, "Macrophages can modify the nonpermissive nature of the adult mammalian central nervous system", Neuron 5:463–469.

Eitan et al., 1994, "Recovery of visual response of injured adult rat optic nerves treated with transglutaminase", Science 264:1764–1768.

Frisen et al., 1994, "Adhesive/repulsive properties in the injured spinal cord: Relation to myelin phagocytosis by invading macrophages", Exp Neurol 129:183–193.

George and Griffin, 1994, "Delayed macrophage responses and myelin clearance during Wallerian degeneration in the central nervous system: The dorsal radiculotomy model", Exp Neurol 129:225–236.

Giulian and Robertson, 1990, "Inhibition of mononuclear phagocytes reduces ischemic injury in the spinal cord", Ann Neurol 27:33–42.

Griffin et al., 1992, "Macrophage responses and myelin clearance during Wallerian degeneration: Relevance to immune mediated demyelination", J Immunol 40:153–166.

Hirschberg et al., 1994, "Inflammation after axonal injury has conflicting consequences for recovery of function: Rescue of spared axons is impaired but regeneration is supported", J Neuroimmunol 50:9–16.

Hirschberg et al., 1995, "Bidirectional communication between the macrophage and the nerve after injury", 9th Int'l Cong. Immunology, San Francisco (Abstract No. 1646).

Khan and Wigley, 1994, "Different effects of a macrophage cytokine on proliferation in astrocytes and Schwann cells", NeuroReport 5:1381–1385.

Lotan and Schwartz, "1994, Cross talk between the immune system and the nervous system in response to injury: Implications for regeneration", FASEB J 8:1026–1033.

Lotan et al., 1994, "Cytokines modulate the inflammatory response and change permissiveness to neuronal adhesion in injured mammalian central nervous system", Exp Neurol 126:284–290.

Mallat et al., 1989, "Lipopolysaccharide–stimulated rat brain macrophages release NGF in vitro", Develop Biol 133:309–311.

Pennell et al., 1995, "Depletion of major histocompatibility complex (MHC)–bearing cells from embryonic rat spinal cord", Society for Neuroscience Abstracts 21:823 (Abstract No. 330.18).

Perry and Brown, 1992, "Role of macrophages in peripheral nerve degeneration and repair", BioEssays 14(6):401–406.

Rabchevsky et al., 1993, "Transplantation of fluorescently–labeled microglia into the adult rat spinal cord", Society for Neuroscience Abstracts 19:57 (Abstract No. 32.14).

Rabchevsky et al., 1994, "Intraspinal transplantation of enriched microglia seeded within biodegradable polymeric tubes: Evidence for neuritic ingrowth", Society for Neuroscience Abstracts 20:879 (Abstract No. 367.11).

Rabchevsky et al., 1995, "Transplantation of brain macrophages (BrM) embedded in gelfoam into the injured rat spinal cord: Evidence for neuritic ingrowth and the presence of extracellular matrix", J. Neurotrauma 12:136 (Abstract).

Rabchevsky, (publication date unknown), "Intraspinal transplantation of microglia: Studies of host cellular responses and effects on neuritic growth", Ph.D. dissertation, University of Florida.

Schwartz, 1987, "Molecular and cellular aspects of nerve regeneration", CRC Critical Rev Biochem 22(2):89–110.

Schwartz et al., 1989, "Dichotomy of the glial cell response to axonal injury and regeneration", FASEB J 3:2371–2378.

Schwartz, 1993, "New light on nerve regeneration in the mammalian nervous system", Endeavour 17(1):38–40.

Schwartz et al., 1994, "Cytokines and cytokine–related substances regulating glial cell response to injury of the central nervous system", Progress in Brain Research 103:331–341.

Schwartz et al., 1995, "Central nervous system regeneration and the immune system", Molec. Medicine Today 1:60.

Schwartz et al., 1995, "CNS repair, remyelination and growth factors" J. Neuroimmunology 0 (Suppl. 1):11 (Abstract).

Sivron et al., 1991, "Soluble factor(s) produced in injured fish optic nerve regulate the postinjury number of oligodendrocytes: Possible role of macrophages", GLIA 4:591–601.

Sivron and Schwartz, 1994, "Nonpermissive nature of fish optic nerves to axonal growth is due to presence of myelin–associated growth inhibitors", Exp Neurol 130:411–413.

Suzuki, (publication date unknown), "Experimental pathology of developing nervous system", NIH Grant No. R01 NS24453–09, Grant application dated Feb. 25, 1994. (Listed in Federal Research in Progress database).

Suzuki, (publication date unknown), "Experimental pathology of developing nervous system", NIH Grant No. R01 NS24453–04, Grant application dated Jun. 6, 1988 and Jun. 23, 1988. (Listed in Federal Research in Progress database).

Thomas, 1992, "Brain macrophages: Evaluation of microglia and their functions", Brain Res Rev 17:61–74.

Vick et al., 1992, "Role of adult oligodendrocytes in remyelination after neural injury", J Neurotrauma 9(Supp 1):S93–S103.

FIG.3A
FIG.3B 5,800,812

METHODS OF USE OF MONONUCLEAR PHAGOCYTES TO PROMOTE AXONAL REGENERATION

This is a continuation-in-part of co-pending application Ser No. 08/528,845, filed Sep. 15, 1995 (abandoned), the entire disclosure of which is incorporated herein by reference.

TABLE OF CONTENTS
1. FIELD OF THE INVENTION
2. BACKGROUND OF THE INVENTION
3. SUMMARY OF THE INVENTION
4. BRIEF DESCRIPTION OF THE FIGURES
5. DETAILED DESCRIPTION OF THE INVENTION
   5.1 MONONUCLEAR PHAGOCYTES
   5.2 METHODS OF USE
   5.3 ASSAY FOR STIMULATORY TISSUES, CELLS AND BIOLOGICALLY ACTIVE AGENTS
6. EXAMPLE: USE OF MONOCYTES TO PROMOTE AXONAL REGENERATION
   6.1 MATERIALS AND METHODS
      6.1.1 ISOLATION AND CULTURE OF MONOCYTES
      6.1.2 STIMULATION OF MONOCYTES
      6.1.3 OPTIC NERVE TRANSECTION
      6.1.4 ASSAYS FOR AXONAL REGENERATION
         6.1.4.1 RETROGRADE LABELING OF AXONS
         6.1.4.2 ANTEROGRADE LABELING OF AXONS
      6.1.5 ASSAY OF PHAGOCYTIC ACTIVITY
   6.2 RESULTS
      6.2.1 PROMOTION OF AXONAL REGENERATION BY STIMULATED AND NON-STIMULATED MONOCYTES
      6.2.2 AXONAL REGENERATION AFTER TREATMENT WITH VARIOUS DOSES OF SCIATIC NERVE- OR OPTIC NERVE-STIMULATED MONOCYTES
      6.2.3 AXONAL REGENERATION AFTER TREATMENT WITH MONOCYTES STIMULATED WITH RAT SCIATIC NERVE SEGMENTS FOR VARIOUS INTERVALS
      6.2.4 AXONAL REGENERATION AFTER TREATMENT WITH MONOCYTES STIMULATED WITH RAT OR MOUSE SCIATIC NERVE SEGMENTS
      6.2.5 PHAGOCYTIC ACTIVITY OF MONOCYTES FOLLOWING CULTURE WITH SEGMENTS OF RAT SCIATIC NERVE
      6.2.6 PHAGOCYTIC ACTIVITY OF MONOCYTES FOLLOWING CULTURE WITH SEGMENTS OF RAT OPTIC NERVE
      6.2.7 PHAGOCYTIC ACTIVITY OF MONOCYTES FOLLOWING CULTURE WITH SCIATIC NERVE SEGMENTS IN THE PRESENCE OF OPTIC NERVE-CONDITIONED MEDIUM
   6.3 DISCUSSION

1. FIELD OF THE INVENTION

The present invention relates to compositions comprising mononuclear phagocytes, and to methods for using mononuclear phagocytes, to promote axonal regeneration in mammals affected by injury or disease of the central nervous system, as well as to compositions and methods for enhancing the therapeutic capacity of mononuclear phagocytes to promote axonal regeneration. In particular, the invention relates to (a) pharmaceutical compositions comprising, and methods for administering, stimulated or non-stimulated allogeneic mononuclear phagocytes at or near a site of the mammalian central nervous system affected by injury or disease to promote axonal regeneration, (b) compositions and methods for stimulating mononuclear phagocytes so as to enhance their capacity to promote axonal regeneration, and (c) methods for screening tissues, cells, proteins, peptides and other biologically active agents for their ability to stimulate mononuclear phagocytes for promoting axonal regeneration.

2. BACKGROUND OF THE INVENTION

Following axonal injury, neurons of the mammalian central nervous system (CNS) have a poor capacity for axonal regeneration. By contrast, neurons of the mammalian peripheral nervous system (PNS) have a substantially greater capacity for axonal regeneration. See Schwartz et al., 1989, FASEB J. 3:2371–2378.

The difference between axonal regeneration in the CNS and PNS has been attributed to the cellular environment of the neurons rather than to the neurons themselves. Following neuronal injury, the Schwann cells that surround PNS neurons are modulated so as to become permissive or supportive for axonal regeneration. By contrast, the astrocytes, oligodendrocytes and microglia that surround CNS neurons do not show such modulation and remain unsupportive or inhibitory for axonal regeneration. See Schwartz et al., 1987, CRC Crit. Rev. Biochem. 22:89–110.

This lack of modulation has been correlated with differences in the post-injury inflammatory response. See Perry and Brown, 1992, Bioessays 14:401–406; Lotan and Schwartz, 1994, FASEB J. 8:1026–1033. In particular, the accumulation of mononuclear phagocytes in response to CNS injury is delayed and limited in comparison with the response to injury in the PNS. This limited CNS mononuclear phagocyte response may in turn lead to (1) inefficient removal of the myelin debris that reportedly inhibits axonal regeneration, and (2) suboptimal release of macrophage-derived cytokines that would promote modulation of astrocytes and oligodendrocytes so as to support axonal regeneration.

The above observations have prompted speculation that appropriate modulation of the macrophage response might promote axonal regeneration after CNS injury. In an in vitro system, David et al. showed that when cryostat sections of normal rat optic nerve are co-cultured with mononuclear phagocytes derived from lesions of the rat CNS, the optic nerve sections show enhanced adhesiveness for embryonic chick dorsal root ganglion cells. David et al., 1990, Neuron 5:463–469. Conditioned medium from activated peritoneal macrophages was also effective in promoting adhesiveness of optic nerve sections in this in vitro assay.

However, results derived from in vivo models of CNS injury have revealed that some interventions that enhance the macrophage response to CNS injury do not result in enhanced regeneration. For instance, local injection of either tumor necrosis factor alpha (TNF-α) or colony stimulating factor-1 (CSF-1) enhanced the macrophage response to experimental optic nerve injury. However, only TNF-α, but not CSF-1, increased the permissiveness of the injured optic nerves for neuronal adhesion as assayed in vitro. Lotan et al., 1984, Exp. Neurol. 126:284–290. It has been suggested as one possible explanation that "only appropriately stimulated macrophages can influence neuronal regeneration." Schwartz et al., 1994, Progress Brain Res. 103:331–341, at 338.

In fact, contrary to the teaching of the present invention, other investigators have reported that mononuclear phagocytes might exacerbate damage or limit recovery following CNS injury. Brain macrophages, when stimulated by cytokines, exhibit neurotoxic activity. Chamak et al., 1994, J. Neurosci. Res. 38:221–233. Pharmacological inhibition of mononuclear phagocyte function has been reported to promote recovery in a rabbit model of spinal cord injury. Giulian and Robertson, 1990, Annals Neurol. 27:33–42. It has been suggested that macrophage-derived cytokines may promote formation of glial scars and thereby inhibit axonal regeneration. Khan and Wigley, 1994, NeuroReport 5:1381–1385; Vick et al., 1992, J. Neurotrauma 9: S93–S103.

To the best knowledge of the present inventors, prior to the present invention there has been no suggestion to administer mononuclear phagocytes into the CNS in order to promote axonal regeneration in the CNS.

Citation or identification of any reference in Section 2 (or any other section) of this application shall not be construed as an admission that such reference is available as prior art to the present invention.

3. SUMMARY OF THE INVENTION

The present invention is directed to methods, and compositions, for use of allogeneic mononuclear phagocytes to promote axonal regeneration in the central nervous system of a mammal. The allogeneic mononuclear phagocytes are administered into the CNS at or near a site of injury or disease.

Allogeneic mononuclear phagocytes useful for the methods and compositions of the invention include, but are not limited to, allogeneic monocytes, macrophages and dendritic cells, and autologous monocytes, macrophages and dendritic cells.

The present invention further provides methods, and compositions, for stimulating allogeneic mononuclear phagocytes so as to enhance their capacity to promote axonal regeneration, and methods, and compositions, for use of stimulated allogeneic mononuclear phagocytes to promote axonal regeneration in the central nervous system of a mammal. The mononuclear phagocytes are stimulated by culturing them together with suitable tissue or suitable cells, or by culturing the mononuclear phagocytes in medium that has been conditioned by suitable tissue or suitable cells. Tissues suitable for this purpose include, without limitation, nerve segments, especially segments of peripheral nerve, dermis, synovial tissue, tendon sheath, liver, and other regenerating tissues. Alternatively, the mononuclear phagocytes are stimulated by culturing them in medium to which at least one suitable biologically active agent has been added. Biologically active agents suitable for this purpose include, without limitation, neuropeptides; cytokines, for instance transforming growth factor-β (TGF-β); and neurotrophic factors, for instance neurotrophic factor 3 (NT-3), nerve growth factor (NGF) and brain-derived neurotrophic factor (BDNF). A biologically active protein or peptide may be used in its native or recombinant form.

Moreover, the present invention provides an assay for identifying additional tissues, cells and biologically active agents that are suitable for stimulating mononuclear phagocytes to enhance their capacity to promote axonal regeneration. According to this assay, mononuclear phagocytes are first cultured together with the tissue or cells to be tested, or in medium that has been conditioned by the tissue or cells to be tested or in medium to which has been added the biologically active agent to be tested. The phagocytic activity of the cultured mononuclear phagocytes is then measured. Mononuclear phagocytes with increased phagocytic activity have an enhanced capacity to promote axonal regeneration.

4. BRIEF DESCRIPTION OF THE FIGS.

The present invention may be more fully understood by reference to the following detailed description of the invention, examples of specific embodiments of the invention and the appended figures in which:

FIG. 1 illustrates axonal regeneration in transected optic nerves of rats as detected by retrograde transport of fluorescent dye to retinal ganglion cells (RGCs). See text, Section 6, for experimental details. Shortly after transection, 2 μl of DCCM-1 medium were applied to the site of injury containing no cells (MED); $2.5 \times 10^3 - 1 \times 10^5$ non-stimulated (NS) monocytes; $2.5 \times 10^3 - 1 \times 10^5$ optic nerve-stimulated (OS) monocytes; or $2.5 \times 10^3 - 1 \times 10^5$ sciatic nerve-stimulated (SS) monocytes. Open circles represent individual experimental animals. Solid circles represent animals that showed no labeled RGCs (numbering 7, 7 and 6 in the MED, NS and OS treatment groups respectively). Horizontal lines represent the median value of each treatment group.

Figure 2:
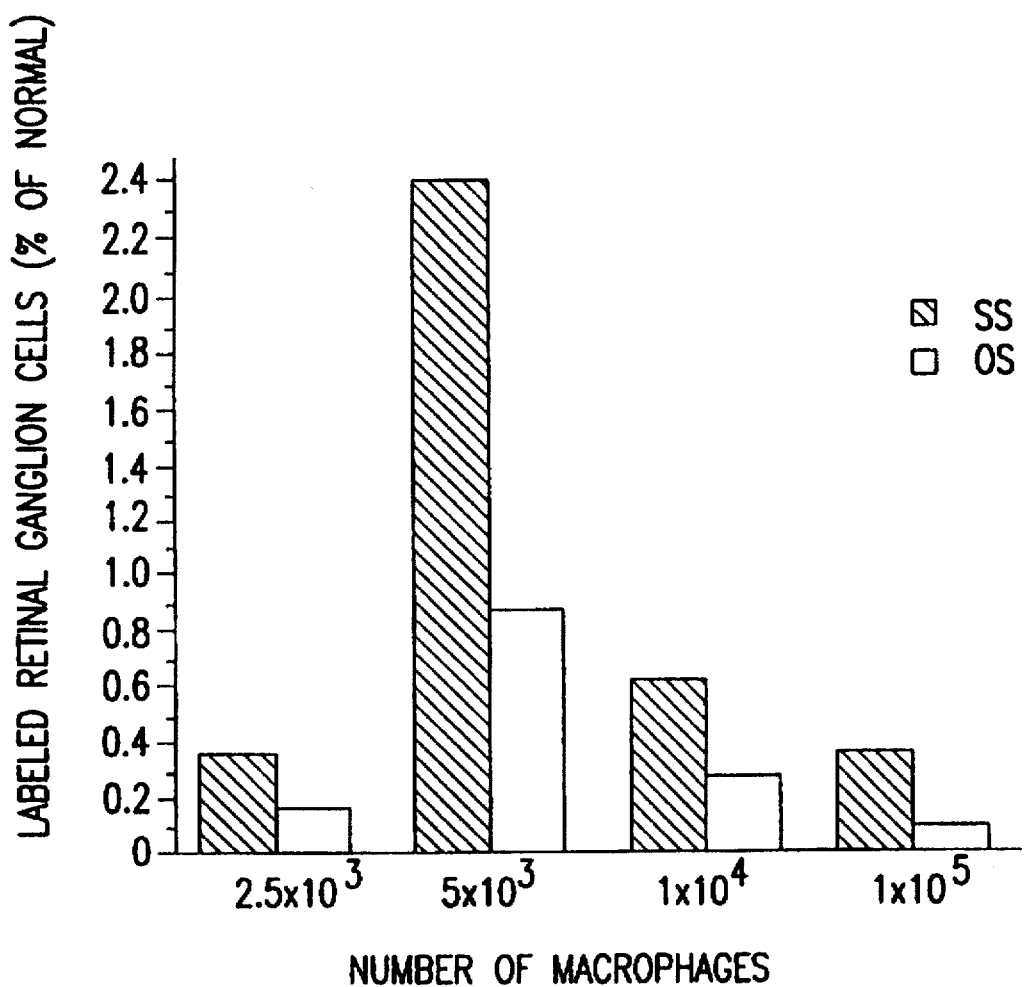
Figure 4A:
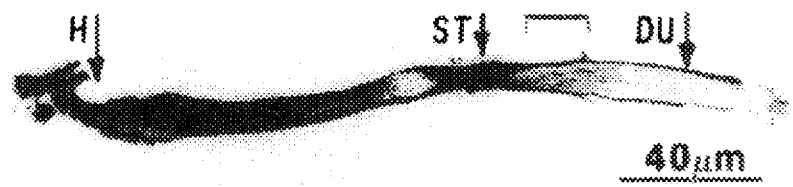
Figure 4B:
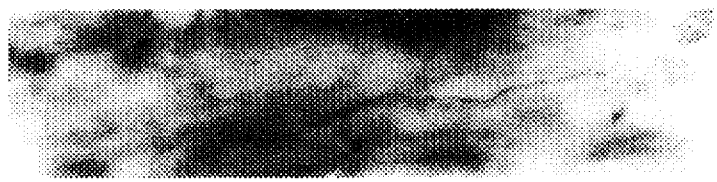
Figure 4C:
Figure 4D:
Figure 4E:
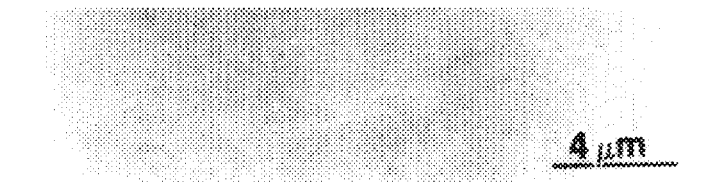

FIG. 2 illustrates axonal regeneration in transected optic nerves of rats as a function of the number and type of monocytes applied to the site of injury shortly after transection. See text, Section 6, for experimental details. At the time of transection, 2 μl DCCM-1 medium were applied to the site of injury containing optic nerve-stimulated monocytes (OS) or sciatic nerve-stimulated monocytes (SS) at a total dose of $2.5 \times 10^3$ cells; $5 \times 10^3$ cells; $10^4$ cells; or $10^5$ cells.

FIG. 3 (A–B) presents representative photomicrographs showing retrograde labeling of retinal ganglion cells in rats subjected to optic nerve transection followed by administration of (A) $5 \times 10^3$ sciatic nerve-stimulated monocytes or (B) control medium. See text, Section 6, for experimental details.

FIG. 4 (A–E) presents representative photomicrographs showing anterograde labeling of optic nerve fibers in rats subjected to optic nerve transection followed by administration of sciatic nerve-stimulated monocytes (A–D) or control medium (E). See text, Section 6, for experimental details. FIG. 4A is a low magnification view showing the point at which HRP was applied (H), the site of transection (ST) and the surrounding dura mater (DU). The bracketed region, distal to the site of transection, is shown at higher magnification in FIGS. 4B, 4C and 4D, in which growth cone-like structures (gc) are shown at the tips of the fibers.

Figure 5:
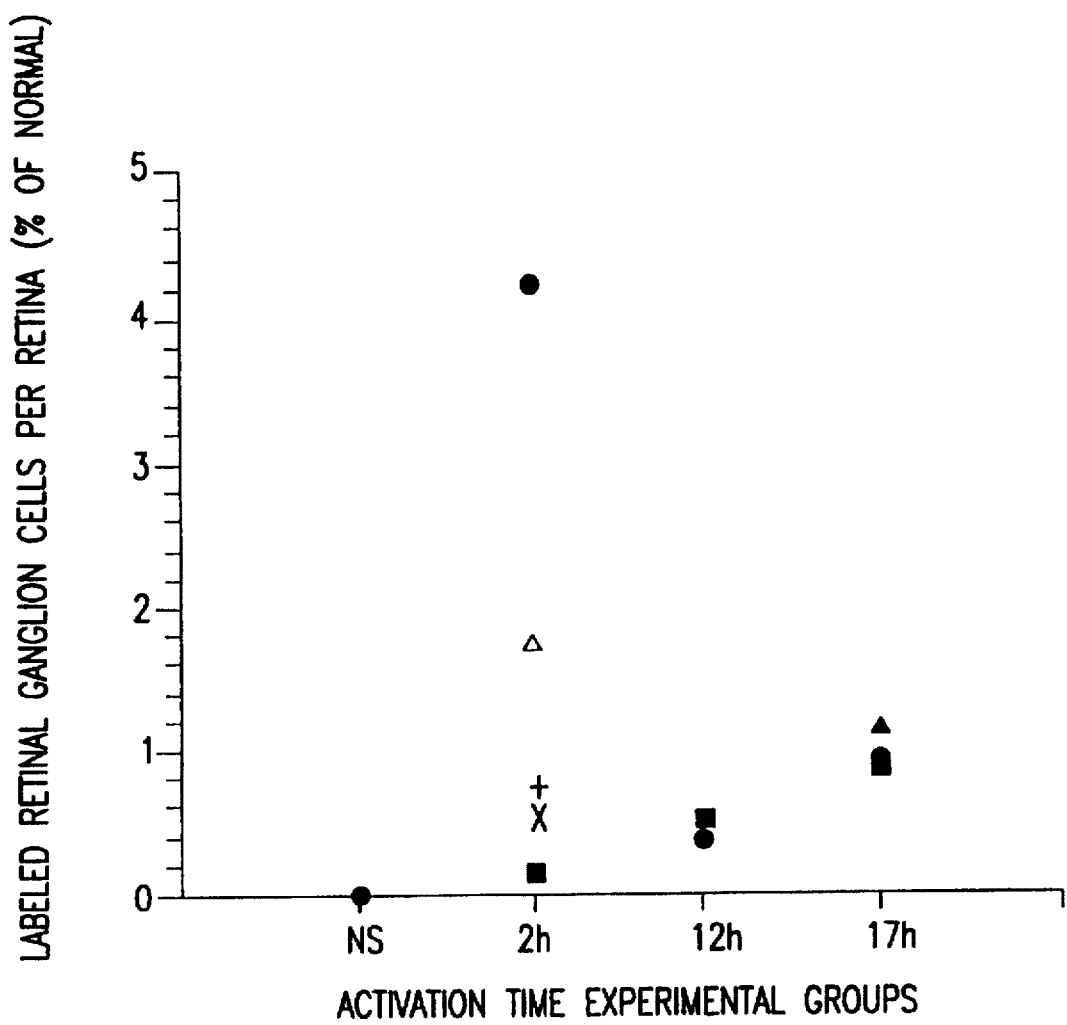

FIG. 5 illustrates axonal regeneration in transected optic nerves of rats after application to the site of injury of monocytes cultured with sciatic nerve for 2–17 hours. See text, Section 6, for experimental details. At the time of transection, 2 μl of DCCM-1 medium were applied to the site of injury containing $5 \times 10^3$ non-stimulated monocytes (NS) or $5 \times 10^3$ monocytes cultured with rat sciatic nerve for 2 hours (2 h), 12 hours (12 h) or 17 hours (17 h).

Figure 6:
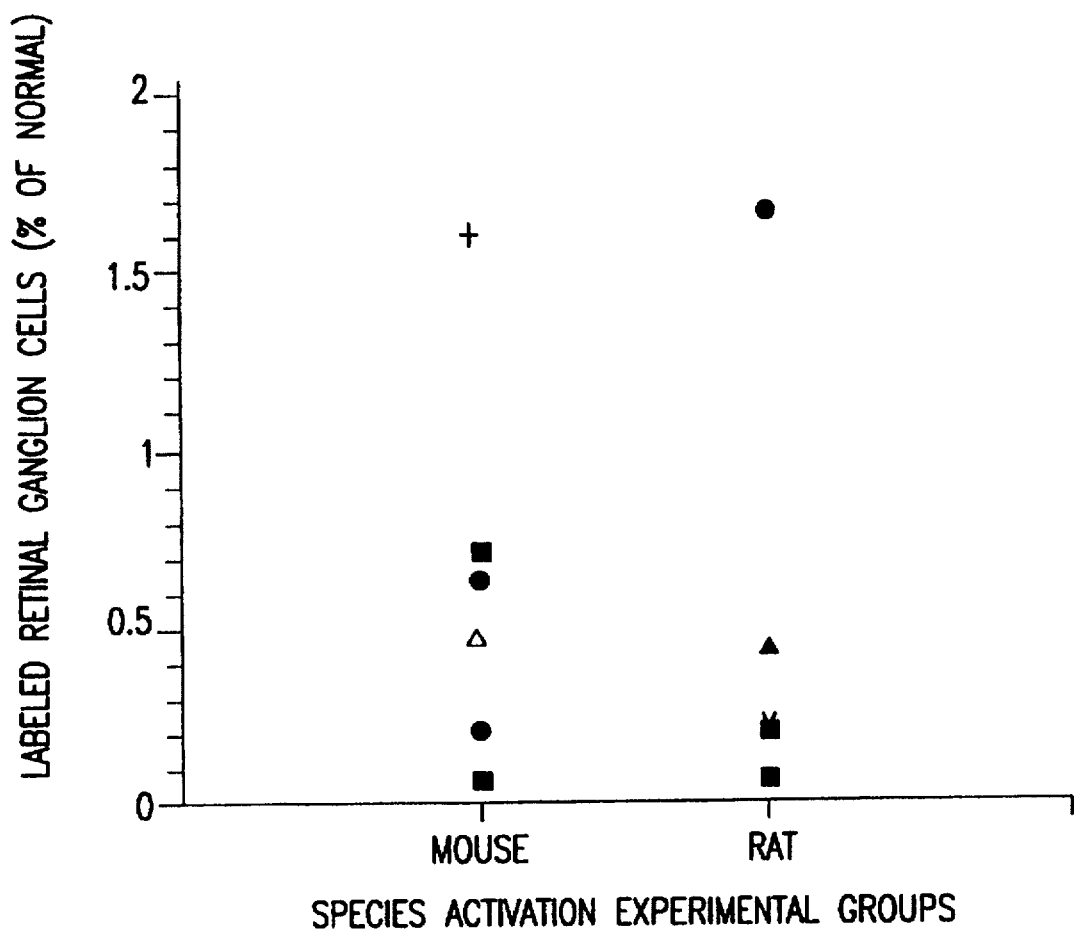

FIG. 6 illustrates axonal regeneration in transected optic nerves after administration, at the site of injury, of rat monocytes stimulated with mouse sciatic nerve or rat sciatic nerve. See text, Section 6, for experimental details. At the time of transection, 2 μl DCCM-1 medium were applied to the site of injury containing $5 \times 10^3$ monocytes cultured for 24 hours with either mouse sciatic nerve (MOUSE) or rat sciatic nerve (RAT).

Figure 7:
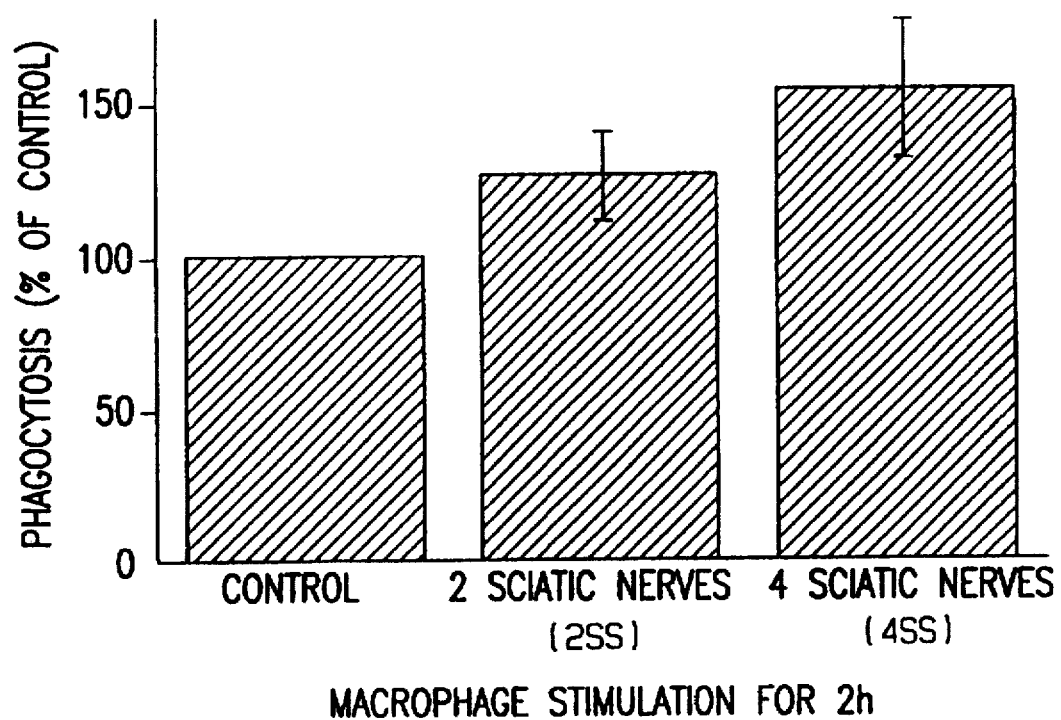

FIG. 7 illustrates the phagocytic activity of rat monocytes cultured for 2 hours with rat sciatic nerve. See text, Section 6, for experimental details. $2.5 \times 10^5$ rat monocytes were cultured in 1 ml DCCM-1 medium alone (CONTROL) or in 1 ml DCCM-1 medium with 2 segments of rat sciatic nerve (2SS) or with 4 segments of rat sciatic nerve (4SS). After 2 hours, the monocytes were exposed to fluorescent beads and cell-associated fluorescence was measured by flow cytometry.

Figure 8:
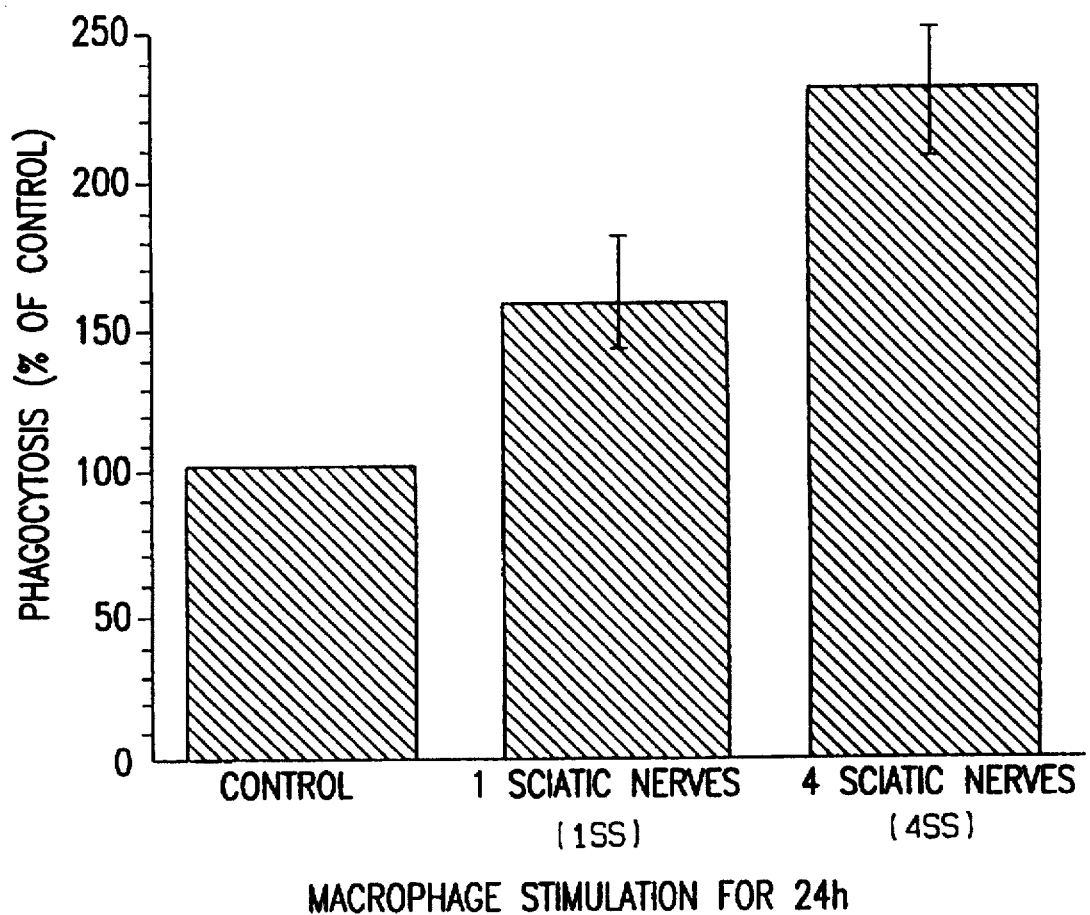

FIG. 8 illustrates the phagocytic activity of rat monocytes cultured for 24 hours with rat sciatic nerve. See text, Section 6, for experimental details. $2.5 \times 10^5$ rat monocytes were cultured in 1 ml DCCM-1 medium alone (CONTROL) or in 1 ml DCCM-1 medium with 1 segment of rat sciatic nerve (1SS) or with 4 segments of rat sciatic nerve (4SS). After 16–24 hours, the monocytes were exposed to fluorescent beads and cell-associated fluorescence was measured by flow cytometry.

Figure 9:
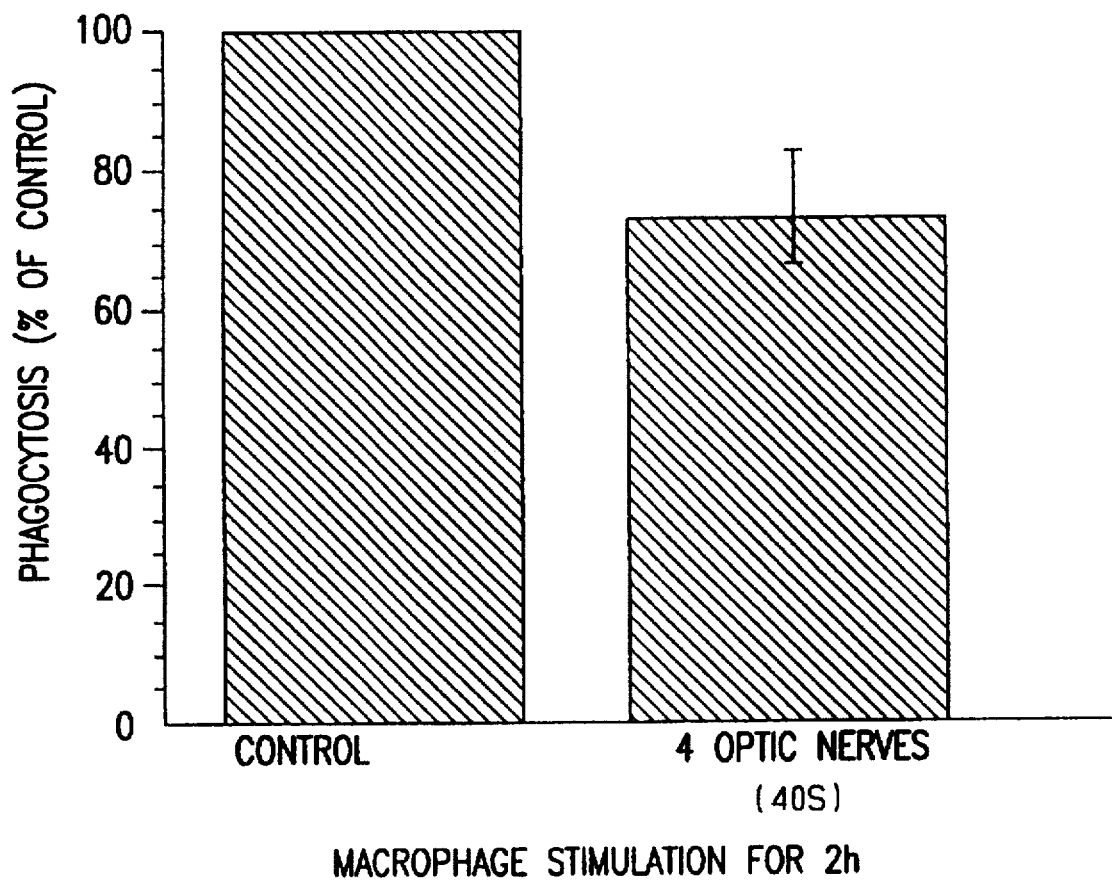

FIG. 9 illustrates the phagocytic activity of rat monocytes cultured for 2 hours with rat optic nerve. See text, Section 6, for experimental details. $2.5 \times 10^5$ rat monocytes were cultured in 1 ml DCCM-1 medium alone (CONTROL) or in 1 ml DCCM-1 medium with 4 segments of rat optic nerve (4OS). After 2 hours, the monocytes were exposed to fluorescent beads and cell-associated fluorescence was measured by flow cytometry.

Figure 10:
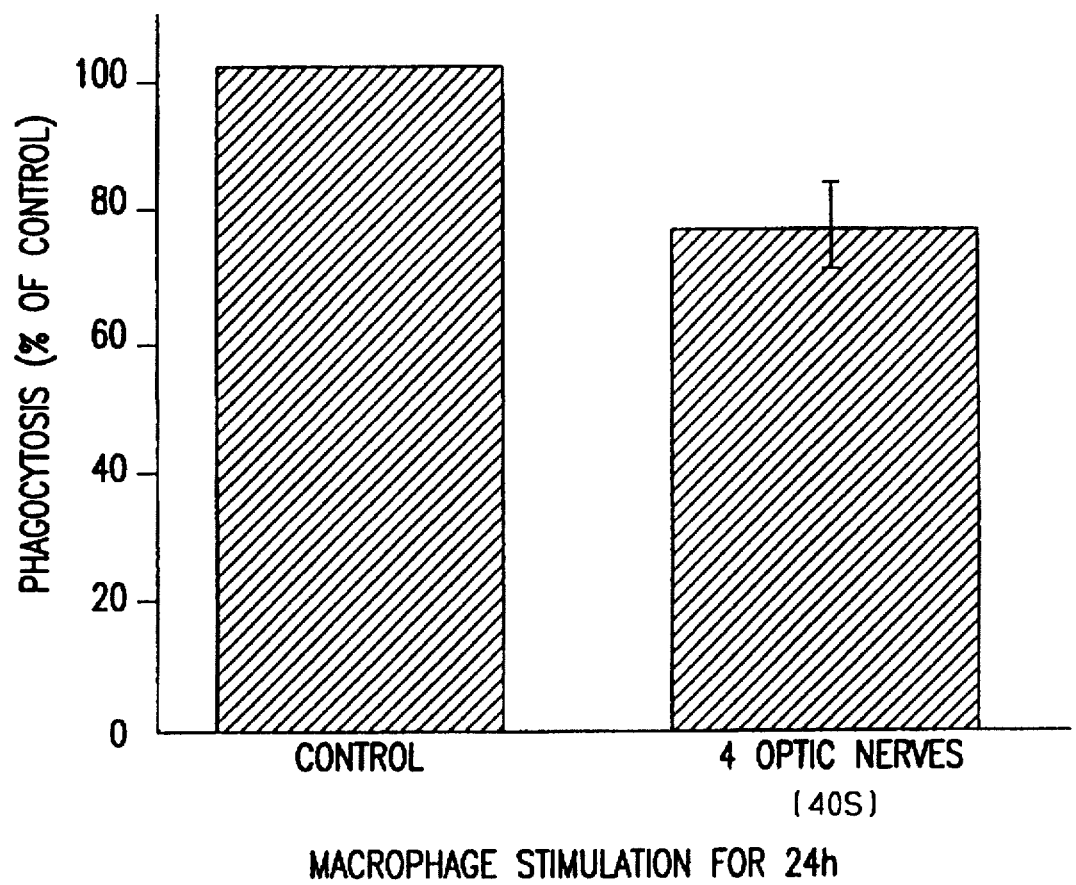

FIG. 10 illustrates the phagocytic activity of rat monocytes cultured for 24 hours with rat optic nerve. See text, Section 6, for experimental details. $2.5 \times 10^5$ rat monocytes were cultured in 1 ml DCCM-1 medium alone (CONTROL) or in 1 ml DCCM-1 medium with 4 segments of rat optic nerve (4OS). After 24 hours, the monocytes were exposed to fluorescent beads and cell-associated fluorescence was measured by flow cytometry.

Figure 11:
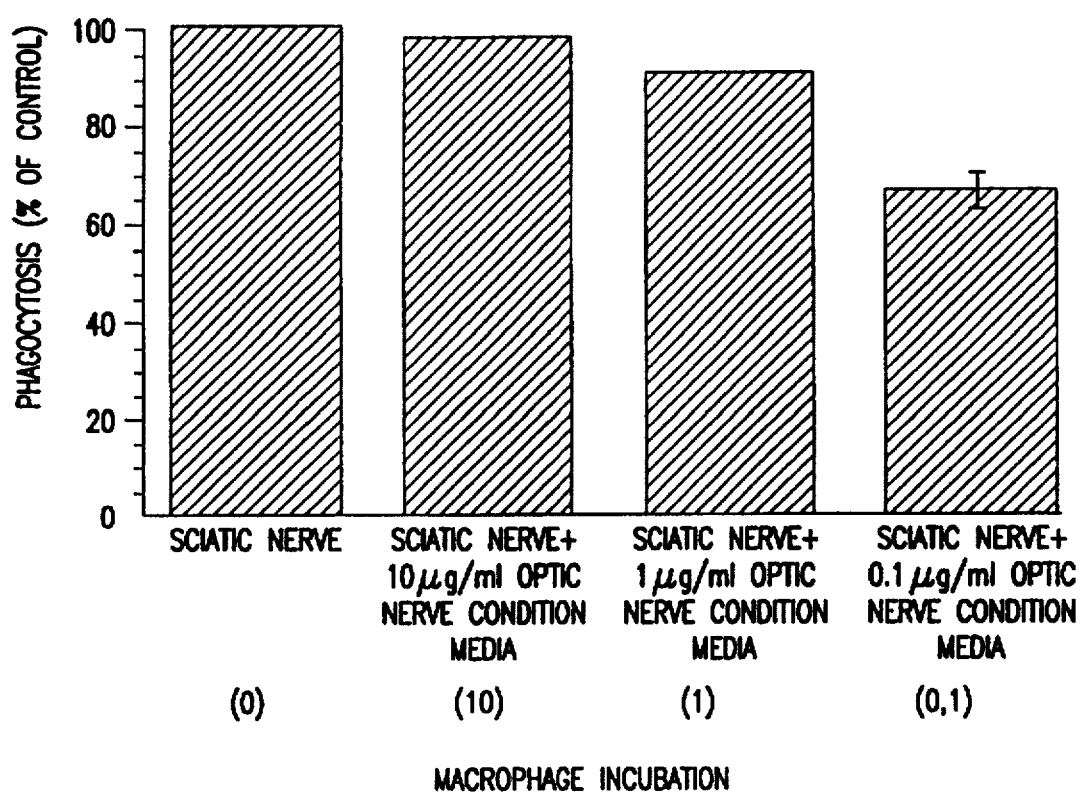

FIG. 11 illustrates the phagocytic activity of rat monocytes cultured overnight with rat sciatic nerve in the presence of medium conditioned by rat optic nerve. $5 \times 10^5$ rat monocytes were cultured in 1 ml DCCM-1 medium with 6 segments of rat sciatic nerve with no further additions (0) or with the addition of optic nerve-conditioned medium at a total protein concentration of 0.1 µg/ml (0.1), 1.0 µg/ml (1), or 10 µg/ml (10). After 24 hours, the monocytes were exposed to fluorescent beads and cell-associated fluorescence was measured by flow cytometry.

5. DETAILED DESCRIPTION OF THE INVENTION

5.1 Mononuclear Phagocytes

The present invention provides methods, and compositions, for use of allogeneic mononuclear phagocytes to promote axonal regeneration following injury or disease of the central nervous system (CNS). The allogeneic mononuclear phagocytes are introduced at or near the site of CNS injury or disease.

As used herein, the term "mononuclear phagocytes" is intended to comprise, without limitation, monocytes obtained from central or peripheral blood, macrophages obtained from any site, including any tissue or cavity, macrophages derived by culturing macrophage precursors obtained from bone marrow or blood, dendritic cells obtained from any site, including spleen, lymph node, skin and lymphatic fluid, and dendritic cells derived from culturing dendritic cell precursors obtained from bone marrow or blood.

Allogeneic mononuclear phagocytes can be obtained from the circulation or from any tissue in which they reside. Peripheral blood is an easily accessible ready source of allogeneic monocytes and is used as a source according to a preferred embodiment of the invention. Especially preferred is the use of autologous monocytes purified from the peripheral blood of a subject to whom the therapeutic preparation is intended to be administered.

Allogeneic mononuclear phagocytes from other sources are well known in the art and include, without limitation, macrophages obtained from serosal cavities such as the peritoneal or pleural cavity, alveolar macrophages, and macrophages associated with other tissues, where they may be known by various terms such as Kupffer cells (in the liver) and microglial cells (in the CNS). Allogeneic mononuclear phagocytes further include dendritic cells, which likewise may be known by various terms, such as Langerhans cells (in the skin), veiled cells (in lymphatic fluid) and interdigitating cells (in lymph nodes). Additionally mononuclear phagocytes can be derived by culture from allogeneic brain-derived mixed glial cells or from allogeneic precursor cells, which may be obtained from bone-marrow or blood.

In a preferred embodiment, cells other than mononuclear phagocytes are depleted from the cell population to be administered. Enrichment techniques are well known to those skilled in the art and include, without limitation, elutriation; centrifugation through material of suitable density, such as a Percoll gradient (Colotta et al., 1983, J. Immunol. 132:936–944); selective adhesion on suitable surfaces followed by removal at reduced temperature or at reduced concentrations of divalent cations (Rosen and Gordon, 1987, J. Exp. Med. 166:1685–1701), mechanical removal, or removal in the presence of lidocaine; and techniques for isolating dendritic cells from blood (O'Doherty et al., 1993, J. Exp. Med. 178:1067–1078), bone marrow (Inaba et al., 1992, J. Exp. Med. 176:1693–1702) and lymphoid tissue (Macatonia et al., J. Exp. Med. 169:1255–1264). Especially preferred is a substantially purified preparation of mononuclear phagocytes.

Once the mononuclear phagocytes are obtained they may be used therapeutically at any desired time, according to the needs of the patient. The mononuclear phagocytes may, if desired, be cultured prior to administration in any suitable culture medium. Preferably, the mononuclear phagocytes are cultured in a vessel made from sterile material to which these cells show limited or no adherence. In a preferred embodiment, the mononuclear phagocytes are cultured in sterile Teflon bags prior to administration.

As used herein, "stimulated" mononuclear phagocytes are mononuclear phagocytes with an enhanced capacity to promote axonal regeneration. Preferably, the capacity of the mononuclear phagocytes to promote axonal regeneration is enhanced at least three-fold over non-stimulated mononuclear phagocytes, more preferably the capacity of the mononuclear phagocytes to promote axonal regeneration is enhanced at least 15-fold over non-stimulated mononuclear phagocytes. "Stimulatory" tissue, cells and biologically active agents are tissue, cells and biologically active agents that, when cultured together with mononuclear phagocytes, enhance the capacity of the mononuclear phagocytes to promote axonal regeneration.

In a preferred embodiment, stimulatory tissue, cells or at least one stimulatory biologically active agent is added to the culture in order to enhance the capacity of the mononuclear phagocytes to promote axonal regeneration. Preferably, one or more segments of a nerve, most preferably a peripheral nerve such as the sciatic nerve, are added to the culture. A xenogeneic nerve is suitable for this purpose or, more preferably, an allogeneic or autologous nerve. If desired, a human nerve can be obtained from any available human tissue, such as a human cadaver or a surgical specimen (e.g. an amputated limb). Alternatively other stimulatory tissue or cells are added to the culture. Dermis is suitable for this purpose and can be obtained, from a living donor or a cadaver, by punch biopsy, by surgical resection, or by any other suitable technique. Synovial tissue, tendon sheath and liver are also suitable for this purpose, as are other regenerating tissues. Additional stimulatory tissues and cells can be identified according to the assay described below. If desired, the stimulatory tissue or cells are homogenized before addition to the culture. As will be evident to those skilled in the art, the stimulatory tissue or cell homogenate can be preserved, e.g. by cryopreservation, before use.

In an alternative embodiment, at least one stimulatory biologically active agent is added to the culture in order to enhance the capacity of the mononuclear phagocytes to promote axonal regeneration. Neurotrophic factor 3 (NT3), nerve growth factor (NGF), brain-derived neurotrophic factor and transforming growth factor-$\beta$ (TGF-$\beta$) are suitable for this purpose either singly or in combination, whether in native or recombinant form. Additional stimulatory biologically active agents (including additional stimulatory proteins and peptides) can be identified according to the assay described below.

Preferably, the mononuclear phagocytes are cultured together with stimulatory tissue, stimulatory cells, homogenate of stimulatory tissue or stimulatory cells, or at least one stimulatory biologically active agent for 24 hours. Shorter periods of culture, such as approximately 2 hours, are also effective, as are longer periods of culture, such as one or more weeks. In an alternative embodiment, stimulatory conditioned medium is prepared by incubating stimulatory tissue or cells, preferably one or more segments of a nerve, most preferably a peripheral nerve such as the sciatic nerve, in any medium that is suitable for culturing mononuclear phagocytes. After removal of the tissue or cells, mononuclear phagocytes are cultured in the stimulatory conditioned medium in order to enhance their capacity to promote axonal regeneration. After removal of the tissue or cells, the stimulatory conditioned medium can be stored and later used as desired for stimulating mononuclear phagocytes. Such stimulatory conditioned medium can be provided in the form of a commercial kit. Preferably, the stimulatory conditioned medium is preserved during storage, for instance by refrigeration, whether as a liquid or as frozen medium. Alternatively, the stimulatory conditioned medium is lyophilized.

As will be evident to those skilled in the art, the mononuclear phagocytes can be preserved, e.g. by cryopreservation, either before or after culture.

Cryopreservation agents which can be used include but are not limited to dimethyl sulfoxide (DMSO) (Lovelock and Bishop, 1959, Nature 183:1394–1395; Ashwood-Smith, 1961, Nature 190:1204–1205), glycerol, polyvinylpyrrolidone (Rinfret, 1960, Ann. N. Y. Acad. Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, Ilbery, P. L. T., ed., Butterworth, London, p. 59), and DMSO combined with hydroxyethel starch and human serum albumin (Zaroulis and Leiderman, 1980, Cryobiology 17:311–317).

A controlled cooling rate is critical. Different cryoprotective agents (Rapatz et al., 1968, Cryobiology 5(1):18–25) and different cell types have different optimal cooling rates. See, e.g., Rowe and Rinfret, 1962, Blood 20:636; Rowe, 1966, Cryobiology 3(I):12–18; Lewis et al., 1967, Transfusion 7(1):17–32; and Mazur, 1970, Science 168:939–949 for effects of cooling velocity on survival of marrow-stem cells and on their transplantation potential. The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve.

After thorough freezing, cells can be rapidly transferred to a long-term cryogenic storage vessel. In one embodiment, samples can be cryogenically stored in mechanical freezers, such as freezers that maintain a temperature of about −80° C. or about −20° C. In a preferred embodiment, samples can be cryogenically stored in liquid nitrogen (−196° C.) or its vapor. Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Considerations and procedures for the manipulation, cryopreservation, and long term storage of hematopoietic stem cells, particularly from bone marrow or peripheral blood, are largely applicable to the mononuclear phagocytes of the invention. Such a discussion can be found, for example, in the following references, incorporated by reference herein: Gorin, 1986, Clinics in Haematology 15(1):19–48; Bone-Marrow Conservation, Culture and Transplantation, Proceedings of a Panel, Moscow, Jul. 22–26, 1968, International Atomic Energy Agency, Vienna, pp. 107–186.

Other methods of cryopreservation of viable cells, or modifications thereof, are available and envisioned for use, e.g., cold metal-mirror techniques. See Livesey and Linner, 1987, Nature 327:255; Linner et al., 1986, J. Histochem. Cytochem. 34(9):1123–1135; see also U.S. Pat. No. 4,199,022 by Senken et al., U.S. Pat. No. 3,753,357 by Schwartz, U.S. Pat. No. 4,559,298 by Fahy.

Frozen cells are preferably thawed quickly (e.g., in a water bath maintained at 37°–41° C.) and chilled immediately upon thawing. It may be desirable to treat the cells in order to prevent cellular clumping upon thawing. To prevent clumping, various procedures can be used, including but not limited to the addition before and/or after freezing of DNAse (Spitzer et al., 1980, Cancer 45:3075–3085), low molecular weight dextran and citrate, hydroxyethyl starch (Stiff et al., 1983, Cryobiology 20:17–24), or acid citrate dextrose (Zaroulis and Leiderman, 1980, Cryobiology 17:311–317), etc.

The cryoprotective agent, if toxic in humans, should be removed prior to therapeutic use of the thawed mononuclear phagocytes. One way in which to remove the cryoprotective agent is by dilution to an insignificant concentration.

Once frozen mononuclear phagocytes have been thawed and recovered, they are used to promote axonal regeneration as described herein with respect to non-frozen mononuclear phagocytes.

5.2 Methods of Use

According to the present invention, the mononuclear phagocytes are suspended in a sterile pharmaceutically acceptable carrier and administered into the CNS of a mammal, including a human subject, at or near a site of injury or disease.

In a preferred embodiment, the pharmaceutically acceptable carrier is PBS or a culture medium. However, alternative pharmaceutically acceptable carriers will readily be apparent to those skilled in the art.

In a preferred embodiment, the mononuclear phagocytes are administered immediately following CNS injury and are introduced at the site of CNS injury, for example with a glass micropipette. However, the present invention encompasses administration of mononuclear phagocytes at any time following CNS injury or disease and encompasses introduction of the mononuclear phagocytes at or near a site of CNS injury or disease by any neurosurgically suitable technique.

The compositions and methods of the present invention are useful for treating any injury or disease of the CNS that results in or is accompanied by axonal damage. The injury or disease may be situated in any portion of the CNS, including the brain, spinal cord, or optic nerve. One example of such injury or disease is trauma, including coup or countercoup injury, penetrating trauma, and trauma sustained during a neurosurgical operation or other procedure. Another example of such injury or disease is stroke, including hemorrhagic stroke and ischemic stroke. Yet another example of such injury or disease is optic nerve injury accompanying optic neuropathy or glaucoma. Still further examples of CNS injury or disease will be evident to those skilled in the art from this description and are encompassed by the present invention. The compositions and methods of the present invention are useful for treating CNS injury or disease that results in axonal damage whether or not the subject also suffers from other disease of the central or peripheral nervous system, such as neurological disease of genetic, metabolic, toxic, nutritional, infective or autoimmune origin.

The optimal dose of mononuclear phagocytes is proportional to the number of nerve fibers affected by CNS injury or disease at the site being treated. In a preferred embodiment, the dose ranges from about $2.5 \times 10^3$ to about $10^5$ mononuclear phagocytes for treating a lesion affecting about $10^5$ nerve fibers, such as a complete transection of a rat optic nerve, and ranges from about $2.5 \times 10^4$ to about $10^6$ mononuclear phagocytes for treating a lesion affecting about $10^6$ nerve fibers, such as a complete transection of a human optic nerve. More preferably, the dose ranges from about $2.5 \times 10^3$ to about $5 \times 10^4$ mononuclear phagocytes for treating a lesion affecting about $10^5$ nerve fibers and ranges from about $2.5 \times 10^4$ mononuclear phagocytes to about $5 \times 10^5$ mononuclear phagocytes for treating a lesion affecting about $10^6$ nerve fibers. Especially preferred is a dose of about $5 \times 10^3$ mononuclear phagocytes for treating a lesion affecting about $10^5$ nerve fibers and a dose of about $5 \times 10^4$ mononuclear phagocytes for treating a lesion affecting about $10^6$ nerve fibers.

5.3 Assay for Stimulatory Tissues, Cells and Biologically Active Agents

The present invention provides an assay for identifying stimulatory tissues and cells and stimulatory biologically active agents. Mononuclear phagocytes are cultured together with the tissue or cells to be tested, in medium conditioned by the tissue or cells to be tested, or in medium to which the biologically active agent or agents to be tested have been added at various concentrations. Thereafter, the phagocytic activity of the mononuclear phagocytes is measured. Mononuclear phagocytes with increased phagocytic activity have an enhanced capacity to promote axonal regeneration. Preferably, the phagocytic capacity of the mononuclear phagocytes is increased by at least 10 percent, more preferably by at least 25 percent, still more preferably by at least 50 percent.

In one embodiment, phagocytic activity is measured by contacting the mononuclear phagocytes with labeled particles and subsequently determining the amount of label associated with the cells. A wide variety of particles can be used for this purpose, including without limitation latex or polystyrene beads and naturally occurring cells, such as red blood cells, yeast and bacteria. Optionally, the particles can be opsonized, for instance with immunoglobulin or complement. The particles can be labeled with any suitable marker, including without limitation a fluorescent marker (such as fluorescein or rhodamine), a radioactive marker (such as a radioactive isotope of iodine, carbon or hydrogen), and an enzyme. Alternatively, the assay can be performed with unlabeled particles (e.g. red blood cells or yeast); the unlabeled particles are detected by any suitable method, such as microscopically, with or without staining. In a preferred embodiment, the mononuclear phagocytes are first contacted with fluorescent polystyrene beads; cell-associated fluorescence is subsequently measured by flow cytometry.

The assay of the present invention also provides a means of determining the period of culture required in order to stimulate the mononuclear phagocytes. Mononuclear phagocytes are cultured for various periods with stimulatory tissue or cells, in medium conditioned by stimulatory tissue or cells, or in medium to which at least one stimulatory biologically active agent has been added. Thereafter, the phagocytic activity of the mononuclear phagocytes is measured. A period of culture sufficient to increase the phagocytic activity of the mononuclear phagocytes by at least 10 percent, preferably by at least 25 percent, more preferably by at least 50 percent, is sufficient to stimulate their capacity to enhance axonal regeneration.

The following examples are presented for purposes of illustration only and are not intended to limit the scope of the invention in any way.

6. EXAMPLE: USE OF MONOCYTES TO PROMOTE AXONAL REGENERATION

6.1 Materials and Methods 6.1.1 Isolation and Culture of Monocytes

Peripheral blood was pooled from adult Sprague-Dawley (SPD) rats. Monocytes were isolated by fractionation on a one-step Percoll gradient as previously described. F. Colotta et al., 1984, J. Immunol. 132:936–944. The monocyte-enriched fraction was recovered from the Percoll interface, washed once with PBS to remove traces of Percoll, and resuspended at $1 \times 10^6$ cells/ml in DCCM-1 medium (Beit Ha'emek Ltd., Kibbutz Beit Ha'emek, Israel). The cells were cultured in Teflon bags at 37° C. as previously described. Andreesen et al., 1983, J. Immunolog. Meth. 56:295–304. Usually, each bag received 10 ml containing $1 \times 10^7$ cells.

6.1.2 Stimulations of Monocytes

Non-stimulated monocytes (NS) were prepared by culturing isolated monocytes in a Teflon bag, as described above, for 2–24 hours. Sciatic nerve-stimulated monocytes (SS) were prepared by culturing monocytes in a Teflon bag for 2–24 hours together with at least one segment of a rat sciatic nerve. Optic nerve-stimulated monocytes (OS) were prepared by culturing monocytes in a Teflon bag for 2–24 hours together with at least one segment of a rat optic nerve. Each nerve segment was 1.0–1.5 cm long in experiments 6.2.1 and 6.2.2, and was 0.5–1.0 cm long in experiments 6.2.3 to 6.2.7; a constant ratio of 1 nerve segment to $5 \times 10^6$ cultured monocytes was used, except where otherwise noted.

After 2–24 hours in culture, monocytes were centrifuged for 3 minutes at 1000×g, washed once with phosphate buffered saline (PBS), and resuspended in DCCM-1 medium at $1.25 \times 10^6$–$5 \times 10^6$ cells/ml. The monocytes were 95% pure as determined by morphology and by immunocytochemistry with the monoclonal antibody ED1 (Serotec, Oxford, England) as described. Hirschberg et al., 1994, J. Neuroimmunol. 50:9–16.

6.1.3 Optic Nerve Transection

Anesthetized adult SPD rats, 8–9 weeks old, were subjected to optic nerve transection as described. Eitan et al., 1994, Science 264:1764–1768. The left optic nerve was exposed through a small opening in the meninges. A curved glass dissector with a 200 µm tip and a smooth blunt edge was moved across the nerve to create a complete transection 2–3 mm distal to the optic globe, taking care not to damage the peripheral blood vessels. As used herein, the term "distal" means away from the optic globe and towards the brain. Shortly after transection, 2 µl of medium containing cultured monocytes or 2 µl of medium alone were introduced at the site of injury by means of a curved glass micropipette with a 25 µm lumen. The meningeal opening was made about 200 µm from the site of transection, in order to minimize leakage of cells from the site of application.

6.1.4 Assay for Axonal Regeneration 6.1.4.1 Retrograde Labeling of Axons

Seven to eight weeks following transection, the lipophilic neurotracer dye, 4-(4-(didecylamino)styryl)-N-methylpyridinium iodide (4Di-10ASP) (Molecular Probes, Eugene, Oreg. USA) was applied to the injured optic nerve, 2 mm distal to the site of injury. One week after application of the dye, the retina was removed, prepared as a flattened whole mount in 4% paraformaldehyde solution, and examined by fluorescence microscopy to detect and count the number of labeled retinal ganglion cells (RGCs) in the entire retina. Only axons that had regrown past the site of injury to the site at which dye was applied could take up the dye and transport it retrogradely to the retinal ganglion cells.

When applied to rat optic nerves that have not previously been transected, this procedure labels an average of 21,623 RGCs per retina. The results for optic nerves that were subjected to transection are expressed as a percentage of this standard, to control for the efficiency of the 4Di-10ASP labeling technique.

6.1.4.2 Anterograde Labeling of Axons

Seven to eight weeks following transection, a fresh incision was made in the previously transected optic nerve 1 mm proximal to the site of transection. As used herein, "proximal" means towards the optic globe and away from the brain. Horseradish peroxidase (HRP) (type VI-A, Sigma, Tel Aviv, Israel) was introduced through the incision by means of a sterile swab soaked in a 50% (w/v) solution of HRP in PBS. Eight to twelve hours after application of the HRP, the rats were perfused through the carotid artery with PBS followed by 4% paraformaldehyde in PBS as a fixative. The optic nerves were excised, 50 µm longitudinal cryosections were taken and processed for visualization of HRP activity using diaminobenzidine and cobalt intensification as described.

Lavie et al., 1992, Brain Res. 575:1–5.

6.1.5 Assay of Phagocytic Activity

Rat monocytes were suspended in DCCM-1 medium ($2.5 \times 10^5$ cells in 1 ml) and were cultured without further additions or together with the indicated number of rat sciatic or optic nerve segments. To assay phagocytic activity, a working solution of fluorescent noncarboxylated microspheres ("FLUORESBRITE"™, Polysciences, Warrington, Penn., USA, Catalog. No. 17152) was prepared by diluting 1 drop of a stock solution in 10 ml DCCM-1 medium and adding this working solution to the monocyte suspension at a further dilution of 1:100. After three hours at 37° C., the cells were washed once with DCCM-1 medium or with phosphate-buffered saline, and cell-associated fluorescence was measured by flow cytometry (FACS).

6.2 Results 6.2.1 Promotion of Axonal Regeneration by Stimulation and Non-Stimulated Monocytes Rats were subjected to optic nerve transection and treated at the time of injury with control medium or with $2.5 \times 10^3$–$1 \times 10^5$ non-stimulated (NS) monocytes, $2.5 \times 10^3$–$1 \times 10^5$ sciatic nerve-stimulated (SS) monocytes, or $2.5 \times 10^3$–$1 \times 10^5$ optic nerve-stimulated (OS) monocytes.

The number of labeled retinal ganglion cells (RGCs) in rats from each treatment group is shown in FIG. 1 as a percentage of RGCs labeled in normal optic nerves. Rats receiving no cells showed almost no labeling of RGCs. Rats receiving NS monocytes showed labeling of modest numbers of RGCs, while treatment with OS monocytes resulted in labeling of greater numbers of RGCs. In rats receiving SS monocytes, the median number of labeled RGCs was over 5-fold higher than in the rats treated with OS monocytes, and was about 15-fold higher than in the rats treated with NS monocytes.

6.2.2 Axonal Regeneration after Treatment with Various Doses of Sciatic Nerve- or Optic Nerve-Stimulated Monocytes To study regeneration as a function of the dose of monocytes administered, rats were subjected to optic nerve transection and treated at the time of injury with OS monocytes or SS monocytes at a total dose of $2.5 \times 10^3$; $5 \times 10^3$; $1 \times 10^4$; or $1 \times 10^5$ cells.

The average number of labeled retinal RGCs in each treatment group is shown in FIG. 2 as a percentage of RGCs labeled in normal optic nerves. RGC labeling was highest after treatment with $5 \times 10^3$ SS monocytes. Higher or lower doses of SS monocytes promoted axonal regeneration but were less effective. Treatment with OS monocytes similarly promoted axonal regeneration, though less effectively. The peak effect, with both OS and SS monocytes, occurred at a dose of $5 \times 10^3$ monocytes; at higher or lower doses the beneficial effect on axonal regeneration was less marked.

Representative fluorescence micrographs of labeled RGCs in retinas after treatment with SS monocytes or control medium are shown in FIG. 3. The absence of labeled RGCs following treatment with control medium indicates that transection was complete and that the labeled RGCs represent regenerating axons that traversed the site of transection and not merely fibers that escaped the experimental injury.

The photomicrographs in FIG. 4 further verify that regrowth has occurred. In nerves treated with control medium (E) no labeled fibers could be seen distal to the site of HRP application. In nerves treated with SS monocytes (A–D) labeled fibers were seen emerging from the proximal part of the nerve, crossing the site of transection (ST) and extending distally. Structures resembling growth cones (gc) were observed at the tips of these labeled fibers.

6.2.3 Axonal Regeneration after Treatment with Monocytes Stimulated with Rat Sciatic Nerve Segments for Various Intervals To study the capacity of monocytes to promote axonal regeneration after stimulation for various intervals with sciatic nerve segments, rats were subjected to optic nerve injury and treated at the time of injury with $5\times10^3$ monocytes cultured with rat sciatic nerve segments for two hours (2 h), twelve hours (12 h) or seventeen hours (17 h). The number of labeled RGCs in individual rats from each treatment group is shown in FIG. 5 as a percentage of RGCs labeled in normal optic nerves. Monocytes showed an enhanced capacity to promote axonal regeneration after culture with sciatic nerve segments for each interval tested.

6.2.4 Axonal Regeneration after Treatment with Monocytes Stimulated with Rat or Mouse Sciatic Nerve Segments To compare the ability of sciatic nerve segments derived from rat and mouse to stimulate the capacity of monocytes to promote axonal regeneration, rats were subjected to optic nerve transection and treated at the time of injury with $5\times10^3$ rat monocytes cultured for 24 hours either with 1–8 segments of rat sciatic nerve (RAT) or with 2–16 segments of mouse sciatic nerve (MOUSE). The number of labeled RGCs in individual rats from each treatment group is shown in FIG. 6 as a percentage of RGCs labeled in normal optic nerves. Both rat and mouse sciatic nerve stimulated the capacity of monocytes to promote axonal regeneration.

6.2.5 Phagocytic Activity of Monocytes Following Culture with Segments of Rat Sciatic Nerve Rat monocytes were suspended at $2.5\times10^5$ cells in 1 ml DCCM-1 medium and were cultured for 2–24 hours without further additions (CONTROL), with 1 segment of rat sciatic nerve (1SS), with 2 segments of rat sciatic nerve (2SS), or with 4 segments of rat sciatic nerve (4SS).

The phagocytic activity of the 2SS and 4SS preparations after 2 hours in culture is shown in FIG. 7 relative to the phagocytic activity of CONTROL monocytes. After culture for 2 hours with two segments of sciatic nerve, the monocytes showed increased phagocytic activity; after culture for 2 hours with four segments of sciatic nerve, the monocytes showed a greater increase in phagocytic activity.

The phagocytic activity of the 1SS and 4SS preparations after 24 hours in culture is shown in FIG. 8 relative to the phagocytic activity of CONTROL monocytes. After culture for 24 hours with one segment of sciatic nerve, the monocytes showed increased phagocytic activity; after culture for 24 hours with four segments of sciatic nerve, the increase in phagocytic activity was even greater. The 4SS preparation showed a greater increase in phagocytic activity after 24 hours than after 2 hours.

6.2.6 Phagocytic Activity of Monocytes Following Culture with Segments of Rat Optic Nerve Rat monocytes were suspended at $2.5\times10^5$ cells in 1 ml DCCM-1 medium and were cultured for 2–24 hours without further additions (CONTROL) or with 4 segments of rat optic nerve (4OS). The phagocytic activity of the 4OS preparations after 2 hours in culture is shown in FIG. 9 relative to the phagocytic activity of CONTROL monocytes. After culture for 2 hours with four segments of optic nerve, the monocytes showed a decrease in phagocytic activity.

The phagocytic activity of the 4OS preparations after 24 hours in culture is shown in FIG. 10 relative to the phagocytic activity of CONTROL monocytes. After culture for 24 hours with four segments of optic nerve, the monocytes showed a decrease in phagocytic activity similar to that seen after 2 hours.

6.2.7 Phagocytic Activity of Monocytes Following Culture with Segments Nerves Segments in the Presence of Optic Nerve-Condition Medium Optic nerve conditioned medium was prepared by culturing segments of rat optic nerve for 2 hours in 1 ml DCCM-1 medium. While fresh DCCM-1 medium is protein-free, the optic nerve conditioned medium contained protein. Rat monocytes were suspended at $2.5\times10^5$ cells in 1 ml DCCM-1 medium and were cultured for 24 hours with 1–6 segments of rat sciatic nerve without further additions (0) or with optic nerve conditioned medium at a total protein concentration of 10 µg/ml (10), 1 µg/ml (1) or 0.1 µg/ml (0.1).

FIG. 11 presents the phagocytic activity of monocytes cultured with sciatic nerve in the presence of optic nerve conditioned medium relative to the phagocytic activity of monocytes cultured with sciatic nerve in the absence of optic nerve conditioned medium. Addition of optic nerve conditioned medium attenuated the enhancement in phagocytic activity caused by culture with sciatic nerve. This attenuation was most marked in the preparation that received 0.1 µg/ml optic nerve conditioned medium.

6.3 Discussion

These examples demonstrate that monocytes administered at a site of CNS injury promoted axonal regeneration. All monocytes tested were effective at promoting axonal regeneration. However, monocytes were stimulated (i.e., showed an enhanced capacity to promote axonal regeneration) by culture with a nerve segment, especially with a segment of a peripheral nerve, e.g. sciatic nerve from rat or mouse.

This stimulation was evident after all periods of culture tested, i.e. from 2–24 hours. For treating a total transection of a rat optic nerve, which contains about $10^5$ nerve fibers, optimal results were obtained by administering about $5\times10^3$ monocytes. However, every dose tested showed a beneficial effect on axonal regeneration.

These examples also demonstrate that monocytes show increased phagocytic activity after culture with one or more segments of sciatic nerve. Thus, measurement of phagocytic activity provides a rapid and efficient method of screening tissues and cells for their capacity to stimulate monocytes to promote axonal regeneration.

The present invention is not to be limited in scope by the exemplified embodiments, which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method of promoting axonal regeneration in the central nervous system (CNS) of a mammal comprising administering an effective amount of allogeneic mononuclear phagocytes into the CNS of said mammal at or near a site of injury or disease of the CNS that results in or is accompanied by axonal damage.

2. The method according to claim 1, in which said allogeneic mononuclear phagocytes are administered as a suspension of mononuclear phagocytes in a pharmaceutically acceptable fluid.

3. The method according to claim 1, in which, prior to the step of administering, said allogeneic mononuclear phagocytes are cultured together with at least one stimulatory tissue, with stimulatory cells, with medium conditioned by at least one stimulatory tissue, with medium conditioned by stimulatory cells, or with medium to which at least one stimulatory biologically active agent has been added.

4. The method according to claim 3, in which the step of culturing said allogeneic mononuclear phagocytes is performed in one or more Teflon bags.

5. The method according to claim 3, in which said allogeneic mononuclear phagocytes are cultured together with dermis prior to the step of administering.

6. The method according to claim 3, in which, prior to the step of administering, said allogeneic mononuclear phagocytes are cultured in medium to which has been added neurotrophic factor 3 (NT-3), nerve growth factor (NGF), brain-derived neurotrophic factor (BDNF) or transforming growth factor-$\beta$ (TGF-$\beta$).

7. The method according to claim 1, in which said allogeneic mononuclear phagocytes are allogeneic monocytes.

8. The method according to claim 7, in which said allogeneic monocytes are administered as a suspension of monocytes in a pharmaceutically acceptable fluid.

9. The method according to claim 7, in which said allogeneic monocytes are autologous monocytes.

10. The method according to claim 9, in which said autologous monocytes are cultured prior to the step of administering.

11. The method according to claim 1, in which said allogeneic mononuclear phagocytes are autologous mononuclear phagocytes.

12. The method according to claim 11, in which said autologous mononuclear phagocytes are cultured prior to the step of administering.

13. The method according to claim 1, in which said allogeneic mononuclear phagocytes are allogeneic macrophages obtained from a serosal cavity, allogeneic alveolar macrophages, allogeneic macrophages obtained from the liver, or allogeneic macrophages derived from culturing macrophage precursors obtained from bone marrow or from blood.

14. The method according to claim 1, in which said allogeneic mononuclear phagocytes are allogeneic dendritic cells.

15. The method according to claim 1, in which, prior to the step of administering, said allogeneic mononuclear phagocytes are cultured together with at least one nerve segment or with medium conditioned by at least one nerve segment.

16. The method according to claim 15, in which said nerve segment is a segment of a peripheral nerve.

17. The method according to claim 15, in which said nerve segment is a segment of an allogeneic peripheral nerve.

18. The method according to claim 1, in which said allogeneic mononuclear phagocytes are mononuclear phagocytes other than microglia.

19. The method according to claim 18, in which said allogeneic mononuclear phagocytes are not derived by culture from brain-derived mixed glial cells.

20. The method according to claim 19, in which said mammal does not suffer from neurological disease of genetic origin.

21. The method according to claim 19, in which said allogeneic mononuclear phagocytes are administered into the spinal cord.

22. The method according to claim 19, in which said allogeneic mononuclear phagocytes are administered into the CNS of a human being.

23. The method according to claim 22, in which, prior to the step of administering, said allogeneic mononuclear phagocytes have been cultured together with dermis or at least one segment of a peripheral nerve or together with medium conditioned by dermis or by at least one segment of a peripheral nerve.

24. The method according to claim 9, in which said autologous monocytes are administered into the CNS of a human being.

25. The method according to claim 24, in which, prior to the step of administering, said autologous monocytes have been cultured together with dermis or at least one segment of a peripheral nerve or together with medium conditioned by dermis or by at least one segment of a peripheral nerve.

26. The method according to claim 23, in which said allogeneic mononuclear phagocytes are administered as a suspension of mononuclear phagocytes in a pharmaceutically acceptable fluid.

* * * * *